(12) United States Patent
Kuhn et al.

(10) Patent No.: US 8,703,965 B2
(45) Date of Patent: Apr. 22, 2014

(54) PREPARATION OF SATURATED IMIDAZOLINIUM SALTS AND RELATED COMPOUNDS

(75) Inventors: Kevin Kuhn, Pasadena, CA (US); Robert H. Grubbs, South Pasadena, CA (US)

(73) Assignees: Materia, Inc., Pasadena, CA (US); California Institute of Technology, Pasadena, CA (US)

( * ) Notice: Subject to any disclaimer, the term of this patent is extended or adjusted under 35 U.S.C. 154(b) by 626 days.

(21) Appl. No.: 12/741,568

(22) PCT Filed: Nov. 10, 2008

(86) PCT No.: PCT/US2008/083023
§ 371 (c)(1),
(2), (4) Date: Dec. 23, 2010

(87) PCT Pub. No.: WO2009/062171
PCT Pub. Date: May 14, 2009

(65) Prior Publication Data
US 2011/0087032 A1    Apr. 14, 2011

Related U.S. Application Data

(60) Provisional application No. 61/002,754, filed on Nov. 9, 2007.

(51) Int. Cl.
*C07D 233/06* (2006.01)

(52) U.S. Cl.
CPC ................................. *C07D 233/06* (2013.01)
USPC .................................... 548/354.1; 548/347.1

(58) Field of Classification Search
USPC ........................................ 548/347.1, 354.1
See application file for complete search history.

(56) References Cited

U.S. PATENT DOCUMENTS

| | | |
|---|---|---|
| 3,150,147 A | 9/1964 | Udelhofen |
| 3,954,634 A | 5/1976 | Monson et al. |
| 3,963,683 A | 6/1976 | Gattuso |
| 3,966,805 A | 6/1976 | Seckinger et al. |
| 4,434,008 A | 2/1984 | Dumm et al. |
| 5,077,414 A | 12/1991 | Arduengo, III |
| 7,109,348 B1 | 9/2006 | Nolan |

FOREIGN PATENT DOCUMENTS

JP    S48-98028    12/1973

OTHER PUBLICATIONS

R. Jazzar et al., A New Synthetic Method for the Preparation of Protonated-NHCs and Related Compounds; Journal of Organometallic Chemistry 691 (2006) pp. 3201-3205.
K. Kuhn et al., "A Facile Preparation of Imidazolinium Chlorides"; Organic Letters, 2008, vol. 10, No. 10, pp. 2075-2077.
G. Uray et al., "Zur Kinetik der Bildung von Arylaminomethlenverbin-dungen aus Triethoxymethan, Arylaminen und CH2-aciden Verbindungen in einer Drikomponentenkondensation", Monatshefte für Chemie 112, pp. 627-641 (1981).
Supplementary European Search Report dated Jan. 30, 2012.
International Search Report (ISR) and Written Opinion (WO) of the International Searching Authority, dated Jan. 30, 2009, in International Application No. PCT/US08/83023.
Office Action for European Application No. 08 848 335.9-2117 dated Jan. 29, 2013.
"Notice of Reasons for Rejection" for Japanese Patent Application No. 2010-533321, Japan Patent Office, Jul. 31, 2013.

*Primary Examiner* — Michael Barker
(74) *Attorney, Agent, or Firm* — Nixon Peabody LLP; Jeffrey L. Costellia

(57) ABSTRACT

Methods for the preparation of saturated imidazolinium salts and related compounds that comprises reaction of formamidines with compounds such as dihaloethane and an optional base are disclosed. Alternatively, the imidazolinium salts and related compounds can be prepared in a one-step process without purification of the formamidine reactant. These methods make it possible to obtain numerous imidazolinium salts and related compounds under solvent-free reaction conditions and in excellent yields.

17 Claims, No Drawings

PREPARATION OF SATURATED IMIDAZOLINIUM SALTS AND RELATED COMPOUNDS

CROSS REFERENCE TO RELATED APPLICATIONS

This application claims priority to PCT Application No. PCT/US2008/083023, filed Nov. 10, 2008, which claims priority under 35 U.S.C. §119 to U.S. Provisional Application Ser. No. 61/002,754, filed Nov. 9, 2007, both of which are herein incorporated by reference in their entirety.

STATEMENT REGARDING GOVERNMENT FUNDING

The U.S. Government has certain rights in this invention pursuant to Grant No. GM031332 awarded by National Institutes of Health.

BACKGROUND OF THE INVENTION

During the last decade, the use of N-heterocyclic carbenes (NHCs) as ligands in organometallic complexes has become routine. NHCs, as neutral, two-electron donors with little backbonding character, have replaced phosphines in a variety of applications. See Diez-Gonzalez, S.; Nolan, S. P. *Coord. Chem. Rev.* 2007, 251, 874; Herrmann, W. A., *Angew. Chem., Int. Ed.* 2002, 41, 1290. Particularly, their use as ligands in ruthenium-based olefin metathesis has allowed for great gains in both activity and stability. Scholl, M.; Ding, S.; Lee, C. W.; Grubbs, R. H. *Org. Lett.* 1999, 1, 953. There is also increasing interest in NHCs as nucleophilic reagents and organocatalysts, with wide use in condensation reactions such as the benzoin condensation, among others. Marion, N.; Diez-Gonzalez, S.; Nolan, S. P. *Angew. Chem., Int. Ed.* 2007, 46, 2988.

Because saturated free carbenes are sensitive toward oxygen and moisture, they are, in most applications, prepared in situ via the deprotonation of their corresponding imidazol(in)ium salts (Equation 1, where the R groups refer to alkyl and aryl groups known in the art for NHC ligands). Therefore, facile and high yielding methods for the synthesis of imidazol(in)ium salts are of great interest.

Equation 1

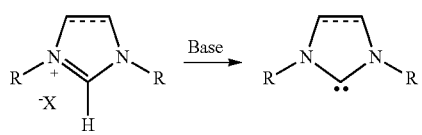

The synthesis of unsaturated imidazolium salts has been optimized and they are now easily prepared by a one step procedure starting from glyoxal, substituted aniline, formaldehyde and an acid. Arduengo, A. J., III, Preparation of 1,3-Disubstitutedlmidazolium Salts, 1991, U.S. Pat. No. 5,077,414. Unfortunately, the preparation of saturated imidazolinium salts still requires several synthetic transformations, including either a palladium-catalyzed C—N coupling or a reduction (Equation 2, where the R groups refer to the hydrocarbyl, or substituted hydrocarbyl groups in U.S. Pat. No. 5,077,414).

Equation 2

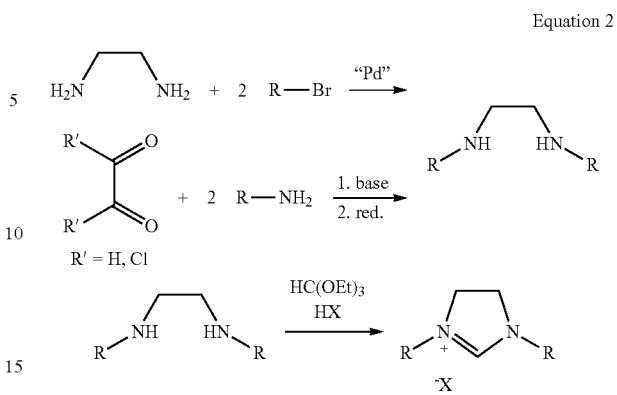

A new pathway to prepare unsaturated imidazolinium salts was developed starting from the addition of a compound featuring two leaving groups to lithiated formamidines. Jazzar, R; Liang, H; Donnadieu, B; Bertrand, G. *Journal of Organometallic Chemistry* 2006, 691 3201. However, the cyclization reaction of the formanidine to the final imidazolinium requires an additional reflux in THF (Equation 3).

Equation 3

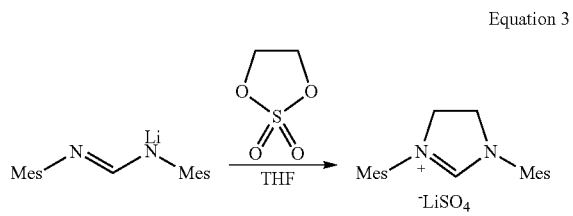

There remains a need in the art to provide improved methods for the preparation of saturated imidazolinium salts and similar compounds from commercially available substituted anilines, naphthylamines, or anthracenylamines. This invention answers that need.

SUMMARY OF THE INVENTION

The invention relates to methods of preparing a compound of formula (III). In this method, a formamidine of formula (I) is reacted with a compound of formula (II) under conditions sufficient to form a compound of formula (III), according to reaction Scheme 1:

Scheme 1

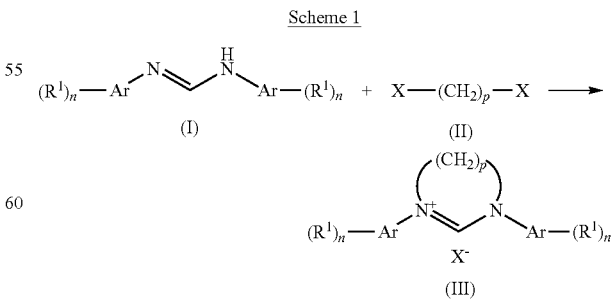

The method may also include the step of preparing the formamidine of formula (I) by the reaction of Scheme 2:

Scheme 2

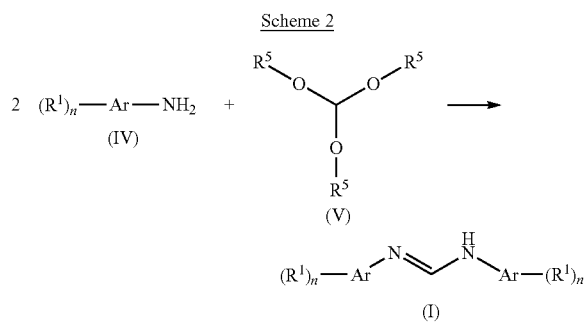

Each Ar in Schemes 1 and 2 may be the same or different. When compounds of formula (IV) having different Ar groups are used in a reaction of Scheme 2, the compounds of formula (IV) are reacted sequentially with the trialkyl orthoformate of formula (V), resulting in a formamadine of formula (I) having different Ar groups.

The invention also relates to a method of preparing a compound of formula (III) according to reaction Scheme 3. In this method, a compound of formula (IV) is reacted with a trialkyl orthoformate of formula (V) in the presence of a compound of formula (II) under conditions sufficient to form a compound of formula (III). A one-step synthesis of a compound of formula (III) may be used when the Ar groups are the same.

Scheme 3

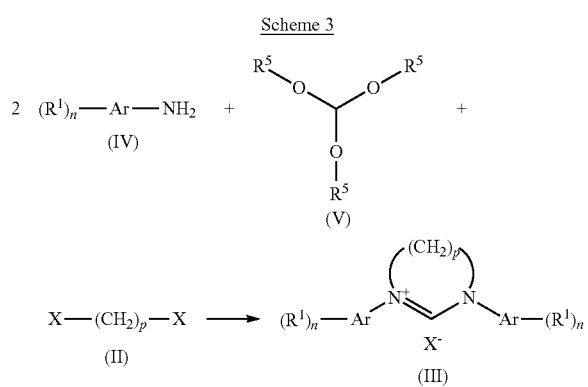

The variables $R^1$, $R^5$, Ar, n, p, and X in Schemes 1, 2 and 3 are defined below.

In certain embodiments, the inventive methods relate to the preparation of symmetric and unsymmetric saturated imidazolinium chlorides by the reaction of a formamidine with dichloroethane (DCE) and a non-nucleophilic base, B, (Equation 4-a). Alternatively, symmetric imidazolinium chlorides can be prepared from substituted anilines without purification of the formamidine (Equation 4-b). In other embodiments, dibromoethane may also be used in place of DCE.

Equation 4 a)

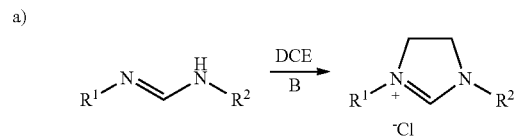

b)

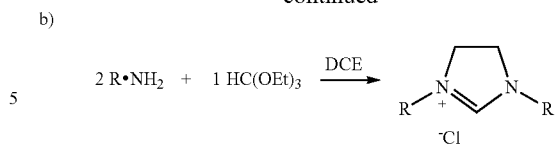

The methods of the invention make it possible to obtain a variety of compounds of formula (III), including imidazolinium chlorides, under solvent-free reaction conditions and in excellent yields. As described below, numerous symmetric and unsymmetric compounds of formula (III) with a variety of N-aryl substituents have been prepared and isolated.

DETAILED DESCRIPTION OF THE INVENTION

In one embodiment, the invention relates to a method of preparing a compound of formula (III). In this method, a formamidine of formula (I) is reacted with a compound of formula (II) under conditions sufficient to form a compound of formula (III), according to reaction Scheme 1:

Scheme 1

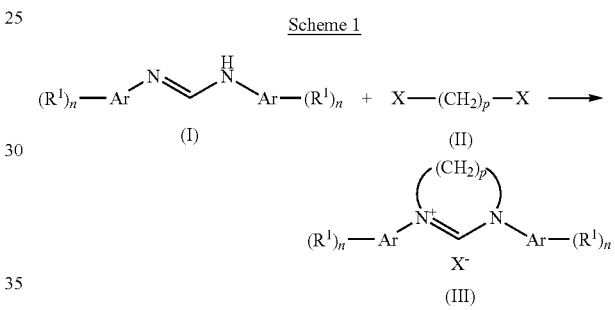

In Scheme 1, each Ar is aryl group, each Ar being independently selected from the group consisting of phenyl, naphthyl and anthracenyl. The Ar group in each occurrence may be the same or different. In certain embodiments, the Ar groups are phenyl.

$R^1$ defines substituents on Ar and may be the same or different in each occurrence even as to substituents on the same aryl groups. $R^1$ in each occurrence is independently selected from the group consisting of $C_1$-$C_6$ alkyl; $C_1$-$C_6$ alkoxy; halogen; aryl; —Si$(R^2)_3$, wherein each $R^2$ is independently a $C_1$-$C_6$ alkyl; and —NR$^3$R$^4$, wherein $R^3$ and $R^4$ are independently a $C_1$-$C_6$ alkyl or wherein $R^3$ and $R^4$, together with the nitrogen carrying them form a 5- or 6-membered heterocyclic ring. The alkyl, alkylene, or alkoxy chains for $R^1$, as well as for any alkyl, alkylene, or alkoxy groups may be straight chain or branched. The aryl group in $R^1$ may be substituted or unsubstituted. Common substituents may be selected from those known in the art, including but not limited to $C_1$-$C_6$ alkyl; $C_1$-$C_6$ alkoxy; halogen; nitro; sulfate; —Si$(R^2)_3$, wherein each $R^2$ is independently a $C_1$-$C_6$ alkyl; and —NR$^3$R$^4$, wherein $R^3$ and $R^4$ are independently hydrogen or $C_1$-$C_6$ alkyl.

In certain aspects of the invention, $R^1$ in each occurrence may be independently selected from the group consisting of $C_1$-$C_4$ alkyl; $C_1$-$C_4$ alkoxy; fluorine; chlorine; phenyl; naphtyl; —Si$(R^2)_3$, wherein each $R^2$ is independently a $C_1$-$C_4$ alkyl; and —NR$^3$R$^4$, wherein $R^3$ and $R^4$ are independently a $C_1$-$C_4$ alkyl. In another embodiment, $R^1$ may be methyl, ethyl, iso-propyl, tert-butyl or fluorine. $R^2$, $R^3$ and $R^4$ may be methyl, ethyl, iso-propyl, or tert-butyl.

The variable "n" defines the number of $R^1$ substituents on the Ar groups. The value of n varies with the type of aryl group. For example, n ranges from 0 to 5 when Ar is phenyl, from 0 to 7 when Ar is naphthyl, and from 0-9 when Ar is anthracenyl. When n is 0, the aryl group is unsubstituted. The degree of substitution on an aryl ring typically ranges from 1 to 3. When Ar is a phenyl group, n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring.

Compounds of formula (II) have the formula $X-(CH_2)_p-X$. The variable "p" defines the number of methylene groups and ranges from 2 to 5. In certain embodiments, p is 2 or 3, such that the compounds of formula (III) have a 5- or 6-membered ring. Compounds of formula (III) having a 5-membered ring are called saturated imidazolinium compounds. Such compounds have a saturated methylene chain linking the two ring nitrogens and may be prepared from compounds of formula (II) having a methylene.

For compounds of formula (II), X is a leaving group. In the reaction X is displaced in the formation of the compound of formula (III). Leaving groups known in the art may be used for X. Exemplary leaving groups include, but are not limited to, a halogen, mesylate, tosylate perchlorate, sulfate, or triflate. Chlorine and bromine are exemplary halogens. Although not required, an excess of the compounds of formula (II) may be used relative to the formamidine of formula (I).

In the reaction described in Scheme 1, the formamidine of formula (I) may act as both a reactant and a sacrificial base. When used as a reactant, the formamidine is generally present in less than one fifth of the molar amount of the compound of formula (II), with a molar ratio of formamidine to formula (II) typically ranging from 1:20 to 1:5. When used as a sacrificial base, the formamidine is generally present in less than one fifth of the molar amount of compound of formula (II), with a molar ratio of formamidine to formula (II) typically ranging from 1:10 to 1:5. Alternatively, the reaction can also occur in the presence of a non-nucleophilic base. The non-nucleophilic base is generally present in a slight molar excess compared to the formamidine, typically with a molar ratio of about 1:1 to 2:1. Non-nucleophilic abases known in the art may be used in the reaction of Scheme 1. Exemplary non-nucleophilic bases include, but are not limited to, di-isopropylethylamine (DIPA), 2,6-dimethylpiperidine, 2,2,6,6-tetramethylpiperidine, di-isopropylamine, Li salt of di-isopropylamide, and bis(trimethylsilyl)amine.

The reaction of Scheme 1 may be conducted in the presence or absence of a solvent. Exemplary solvents include nonpolar, aprotic solvents such as diethoxyethane or an aromatic solvent, e.g., toluene, xylene or mesitylene. For a solvent-free synthesis, the compound of formula (II), $X-(CH_2)_p-X$, e.g., dichloroethane (DCE), may act as the solvent. Solvent-free conditions generally provide certain advantages, including reduced expense.

Although not limited thereto, the reaction of Scheme 1 is generally run at a temperature ranging from about 40° C. to about 150° C. and for a time period ranging from about 16 hours to about 168 hours. When compounds of formula (II) are dichloroethane (DCE), a reaction temperature of over 100° C. is typically used. The use of dibromoethane (DBE) formula (II) compounds typically requires a lower reaction temperature than DCE; diiodoethane (DIE) requires even lower reaction temperature than DBE. Increased steric bulk of substituents on the aryl groups of formamidine of formula (I) may result in longer reaction times, while higher temperature or longer reaction time may increase the yield of compounds of formula (III).

In one aspect of the invention, the reaction of Scheme 1 may be carried out under a dry, inert atmosphere. Inert atmospheres, as is known in the art, typically employ inert gases, including such gases as nitrogen and argon. The reactions of the invention may also be carried out in an oxygen-containing and/or water containing atmosphere.

In another aspect in accordance with the reaction of Scheme 1, the invention relates to a process for the preparation of symmetric and unsymmetric saturated imidazolinium chlorides that comprises reaction of a formamidine with dichloroethane (DCE) and a base. Diisopropylethylamine (DIPA) has been found to be an effective base (Table 1, Method A). As discussed above, the formamidine can act as both substrate and sacrificial base in the reaction (Table 1, Method B). Both the imidazolinium chlorides and hydrochloride salt of either base can be isolated by means known in the art, e.g., by sequential precipitation in a solvent such as toluene or acetone. General procedures to isolate and purify imidazolinium salts are described in the examples below. The formamidine salts produced in the reaction may also be regenerated to form formamidine. For example, formamidine hydrochloride can be reverted to formamidine by solvation in pyridine followed by precipitation in water.

TABLE 1

Preparation of 1,3-Diarylimidazolinium Chlorides from Formamidines

Method A $$R^1-N=CH-NH-R^2 \xrightarrow[\text{DIPA}]{\text{DCE}}$$

imidazolinium chloride + DIPA·HCL

Method B $$R^1-N=CH-NH-R^2 \xrightarrow{\text{DCE}}$$

imidazolinium chloride + formamidinium chloride

| Entry | Substituents | | Time (H) | A yield (%) | B yield (%)[a] |
|---|---|---|---|---|---|
| 1 | $R^1$ | 2,4,6-Trimethylphenyl | 24 | 92 | 49 (98) |
|   | $R^2$ | " | | | |
| 2 | $R^1$ | 2-Methylphenyl | 24 | 43 | 48 (96) |
|   | $R^2$ | " | | | |
| 3 | $R^1$ | 2,6-Diisopropylphenyl | 36 | 91 | 46 (92) |
|   | $R^2$ | " | | | |
| 4 | $R^1$ | 2-Tertbutylphenyl | 168[b] | 42 | 19 (38) |
|   | $R^2$ | " | | | |
| 5 | $R^1$ | 2,4,6-Trimethylphenyl | 36 | 75 | 41 (82) |
|   | $R^2$ | 2,6-Difluorophenyl | | | |
| 6 | $R^1$ | 2-Methylphenyl | 24 | 80 | 43 (86) |
|   | $R^2$ | 2,6-Diisopropylphenyl | | | |

[a]Yield in brackets based on a 50% theoretical yield with half of the substrate considered as a sacrificial base.
[b]While neither reaction had reached 100% conversion, the reactions were stopped after 7 days.

The methods of the invention may also include the step of preparing the formamidine of formula (I) by the reaction of Scheme 2:

Scheme 2

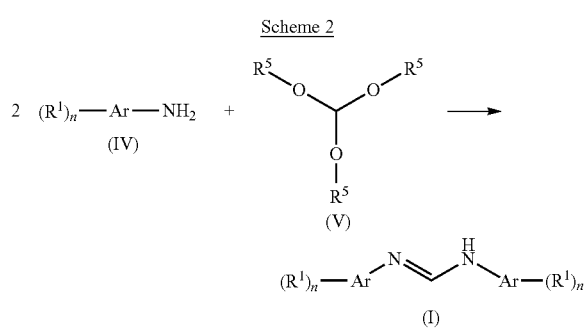

This procedure for preparing formamidines of formula (I) has been described in Roberts, R. M., *J. Org. Chem.* 1949, 14(2), 277 and Kuhn, K. M.; Grubbs, R. H. *Org. Lett.* 2008, 10, 2075.

As noted, each Ar in Scheme 2 may be the same or different. When compounds of formula (IV) having different Ar groups are used in a reaction of Scheme 2 the compounds of formula (IV) are reacted sequentially with the trialkyl orthoformate of formula (V), resulting in a formamadine of formula (I) having different Ar groups.

In Scheme 2, each Ar is independently selected from the group consisting of phenyl, naphthyl and anthracenyl. As in Scheme 1, Ar may be phenyl but, because two moles of the compound of formula (IV) are used, each Ar may be different. When more than one compound of formula (IV) is used, each Ar is different and the compounds of formula (IV) are reacted sequentially with the trialkyl orthoformate of formula (V) prior to reaction with compound (II).

The substituents and variables $R^1$, n, X, and p are the same as described above with reference to Scheme 1.

For the trialkyl orthoformate of formula (V) $R^5$ is a $C_1$-$C_6$ alkyl, and may be a $C_1$-$C_4$ alkyl such as, but not limited to, methyl, ethyl, propyl, iso-propyl or tert-butyl. For example, a triethyl orthoformate, where $R^5$ is ethyl, may be used.

The reaction conditions such as solvent, reaction temperature, reaction time period, reaction atmosphere are the same as described above with reference to Scheme 1.

Another embodiment of the invention relates to a one-step method of preparing a compound of formula (III) according to reaction Scheme 3. In this method, a compound of formula (IV) is reacted with a trialkyl orthoformate of formula (V) in the presence of a compound of formula (II) under conditions sufficient to form a compound of formula (III). The groups Ar are the same in each occurrence.

Scheme 3

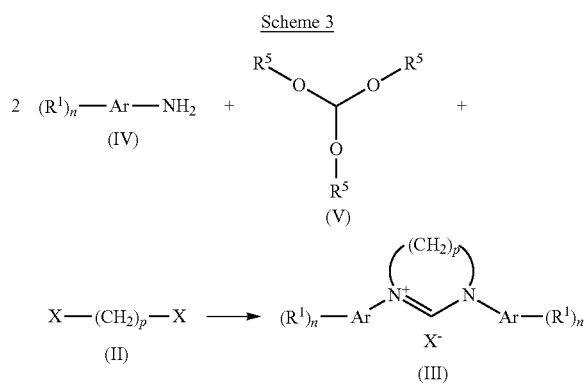

While not limited thereto, one mole of the compounds of formula (V) is generally used in Scheme 3 to react with two moles of the compounds of formula (IV) in the presence of excess amount of the compounds of formula (II). The molar ratio of the compounds of formula (IV) to formula (V) and to formula (II) is typically 2:5:1. The reaction conditions are generally the same as described above for Schemes 1 and 2.

The preparation of symmetric imidazolinium chlorides in a one-step method of the invention is described in Table 2. The formamidine, as base and intermediate, is formed in situ, followed by cyclization to yield the imidazolinium salt.

TABLE 2

Preparation of 1,3-Diarylimidizolinium Chlorides from Substituted Anilines in One-Step 2 R—NH$_2$ + 1 HC(OEt)$_3$ $\xrightarrow{\text{DCE}}$

| Entry | Substituents | | Time (h) | Yield (%)[a,b] |
|---|---|---|---|---|
| 1 | R | 2,4,6-Trimethylphenyl | 24 | 45 (90) |
| 2 | R | 2-Methylphenyl | 24 | 26 (52) |
| 3 | R | 2,6-Diisopropylphenyl | 36 | 42 (84) |

[a]Isolated yield of the desired imidazolinium chloride.
[b]Yield in parentheses based on a 50% theoretical yield with half of the substrate considered as a sacrificial base.

EXAMPLES

The following examples illustrate the various embodiments of the invention and are not to be construed as limiting the scope of the invention. Other aspects, advantages and modifications within the scope of the invention will be apparent to those skilled in the art to which the invention pertains.

Method A describes the preparation of compounds of formula (III) according to Scheme 1 with a non-nucleophilic base. Method B describes the preparation of compounds of formula (III) according to Scheme 1 using the formamidine of formula (I) as a sacrificial base. Method C describes the one-step method of preparation of compounds of formula (III) via Scheme 3.

Method A1: Diisopropylethylamine (1.1 equiv) was added to a stirred solution of formamidine (1 equiv) and dichloroethane (10 equiv) in a schlenk tube. The tube was evacuated until solvent began to bubble and then sealed and heated to 120° C. for 24-168 hours. The reaction mixture was then cooled to room temperature, diluted with solvent (acetone or hot toluene), and the precipitated imidazolinium chloride was collected by vacuum filtration, washed with excess solvent and dried in vacuo. Upon sitting overnight, the Diisopropylethylamine hydrochloride precipitated from the filtrate.

Example 1

According to method A1, diisopropylethylamine (0.34 mL, 1.96 mmol) was added to a stirred solution of N,N'-dimesitylformamidine (0.5 g, 1.78 mmol) and dichloroethane (1.36 mL, 17.8 mmol) in a schlenk tube. The tube was evacuated until solvent began to bubble and then sealed and heated to 120° C. for 24 hours. The reaction mixture was then cooled, added to toluene (40 mL) and then brought to reflux. While still hot, the precipitate was collected by vacuum filtration, washed with toluene (5 mL) and dried in vacuo to afford 1,3-dimesitylimidazolinium chloride (0.56 g, 92%) as a light peach powder.

Example 2

N,N'-dimesitylformamidine (DMFA; 1 equivalent), 1,2-dichloroethane (DCE), and a magnetic stir bar were charged to a 3-neck round-bottomed flask which was fitted with a refluxing condenser and a thermowell. The flask was heated in an oil bath to the desired temperature and diisopropylethylamine (DIPA) was then added. The flask was kept at the temperature for a period of time. DCE was stripped off by distillation. Toluene was added to the mixture, and the flask was allowed to cool. Acetone was added and the solid was collected by filtration. The solid was dried in a vacuum oven at room temperature for 16 h and at 40° C. for 8 h. Experimental conditions and results are summarized in Table 3.

TABLE 3

Synthesis of 1,3-Dimesitylimidazolinium Chloride

| Entry | DMFA (mole) | DCE (mole) | DIPA (mole) | Ratio of DMFA/DCE/DIPEA | Temp. (° C.) | Time (hr) | Yield (%) |
|---|---|---|---|---|---|---|---|
| a | 0.100 | 0.50 | 0.110 | 1/5/1.1 | 100 | 48 | 80 |
| b | 0.050 | 1.00 | 0.057 | 1/20/1.1 | 100 | 24 | 68 |
| c | 0.200 | 4.00 | 0.220 | 1/20/1.1 | 100 | 48 | 87 |
| d | 0.390 | 7.78 | 0.430 | 1/20/1.1 | 100 | 48 | 88 |
| e | 0.036 | 0.36 | 0.040 | 1/10/1.1 | 120 | 24 | 58.0 |
| f | 0.053 | 0.53 | 0.064 | 1/10/1.2 | 120 | 24 | 60.5 |
| g | 0.200 | 3.00 | 0.240 | 1/15/1.2 | 120 | 24 | 74.3 |
| h | 0.050 | 1.00 | 0.055 | 1/20/1.1 | 120 | 24 | 76.0 |

Example 3

N,N'-Dimesitylformamidine (DMFA; 1 equivalent), 1,2-dibromoethane (DBE; 5 equivalents), and a magnetic stir bar were charged to a 3-neck round-bottomed flask which was fitted with a reflux condenser and thermowell. The flask was heated in an oil bath to the desired temperature and diisopropylethylamine (DIPA; 1.1 equivalents) was then added. The flask was kept at temperature for a period of time. The excess DBE was stripped off under vacuum and the flask was allowed to cool to room temperature. Acetone was added with careful stirring to break up the resultant solid mass. The slurry was filtered and the recovered solid was washed with acetone. The solid was dried in a vacuum oven at room temperature for 16 h and at 40° C. for 8 h.

Experimental conditions and results are summarized in Table 4.

TABLE 4

Synthesis of 1,3-Dimesitylimidazolinium Bromide

| Entry | DMFA (mole) | DBE (mole) | DIPA (mole) | Temp. (° C.) | Time (hrs) | Yield (%) |
|---|---|---|---|---|---|---|
| a | 0.09 | 0.45 | 0.10 | 100 | 16 | 85 |
| b | 0.10 | 0.50 | 0.11 | 90 | 72 | 88 |

Example 4

N,N'-Dimesitylformamidine (2.8 g, 10 mmol), 1,3-dibromopropane (10.0 g, 50 mmol), and a magnetic stir bar were charged to a 50-mL round-bottomed flask which was fitted with a reflux condenser and connected to a nitrogen bubbler. The flask was placed in an oil bath, and diisopropylethylamine (1.42 g, 11 mmol) was added when the oil temperature reached 110° C. The temperature of the oil bath was then raised to 130° C. for 3.5 hours. The mixture was cooled and volatiles (primarily 1,3-dibromopropane) were removed under vacuum. The resulting solid was identified as the desired 1,3-dimesityltetrahydropyrimidinium bromide by $^1$H NMR analysis. $^1$H NMR (CDCl$_3$): δ 7.55 (s, NCHN, 1H), 6.92 (s, Me$_3$C$_6$H$_2$, 4H), 4.19 (t, NCH$_2$CH$_2$CH$_2$N, $\overline{4H}$), 2.57 (m, NCH$_2$CH$_2$CH$_2$N, 2H), 2.32 (s, o-$\overline{CH_3}$, 12H), 2.25 (s, p-CH$_3$, 6H).

Example 5

N,N'-Dimesitylformamidine (DMFA; 0.10 mole, 1 equivalent), 1,2-dibromoethane (DBE), solvent, and a magnetic stir bar were charged to a 3-neck round-bottomed flask which was fitted with a reflux condenser and thermowell. The flask was heated in an oil bath to 110° C. (in case of toluene, 100° C.) and diisopropylethylamine (DIPA; 0.11 mole, 1.1 equivalents) was then added. The flask was kept at 110° C. for 16 hours. For entry a and b the excess DBE (entry a and b) was stripped off under vacuum. For entry c through e the stripping step was skipped. The flask was allowed to cool to room temperature. Acetone was added and the solid was filtered and washed with acetone. The solid was dried in a vacuum oven at room temperature for 16 h and at 40° C. for 8 h. Experimental conditions and results are summarized in Table 5.

TABLE 5

Synthesis of 1,3-Dimesitylimidazolinium Bromide

| Entry | DBE (mole) | DBE (equiv.) | Solvent | Solvent/DMFA (wt./wt.) | Yield (%) |
|---|---|---|---|---|---|
| a | 0.30 | 3.0 | Xylenes | 1/1 | 86 |
| b | 0.15 | 1.5 | Xylenes | 1/1 | 88 |
| c | 0.11 | 1.1 | Xylenes | 1.4/1 | 80 |
| d | 0.11 | 1.1 | Xylenes | 1.4/1 | 86 |
| e | 0.11 | 1.1 | Toluene | 1.4/1 | 85 |

Method B1: Dichloroethane (10 equiv) was added to a schlenk flask charged with formamidine (2 equiv). The tube was evacuated until solvent began to bubble and then sealed and heated with stirring to 120° C. for 24 hours. The reaction mixture was then cooled to room temperature, diluted with solvent (acetone or hot toluene), and the precipitated imidazolinium chloride was collected by vacuum filtration, washed with excess solvent and dried in vacuo. Upon sitting overnight, the formamidine hydrochloride precipitated from the filtrate.

Example 6

According to method B1, dichloroethane (1.36 mL) was added to a schlenk flask charged with N,N'-dimesitylformamidine (0.5 g, 1.78 mmol). The tube was evacuated until solvent began to bubble and then sealed and heated with stirring to 120° C. for 24 hours. The reaction mixture was then cooled, added to toluene (40 mL) and then brought to reflux. While still hot, the precipitate was collected by vacuum filtration, washed with toluene (5 mL) and dried in vacuo to afford 1,3-dimesitylimidazolinium chloride (0.3 g, 49%) as a light peach powder.

The filtrate was allowed to sit overnight to allow for precipitation of N,N'-dimesitylformamidine hydrochloride. The precipitate was collected by vacuum filtration, washed with hexanes (5 mL) and dried in vacuo to afford N,N'-dimesitylformamidine hydrochloride (0.27 g, 48%) as colorless crystals.

Example 7

Symmetric formamidines can be prepared according to the method described below. Acetic acid (0.05 equiv) was added to a round bottom flask charged with substituted aniline (2 equiv) and triethyl orthoformate (1 equiv). The solution was heated with stirring to 120-160° C. for 4-12 hours and cooled to room temperature, whereupon crude formamidine precipitated. Trituration with cold hexanes and vacuum filtration provided pure formamidine as a colorless powder (85-95%).

Example 8

Acetic acid (0.15 mL, 2.67 mmol) was added to a round bottom flask charged with 2,4,6-trimethylaniline (15 mL, 106.7 mmol) and triethyl orthoformate (8.88 mL, 53.36 mmol). A vigreux column was attached and the solution was heated with stirring to 120° C. for 4 hours and cooled to room temperature, whereupon crude product precipitated. Trituration with cold hexanes and vacuum filtration provided pure N,N'-dimesitylformamidine (13.77 g, 92%) as a colorless powder.

Example 9

Unsymmetric formamidines can be prepared according to the method described below. Acetic acid (0.05 equiv) was added to a round bottom flask charged with a substituted aniline (1 equiv) and triethyl orthoformate (1 equiv). The solution was heated with stirring to reflux for 2 hours and then a second substituted aniline (1 equiv) was added to the reaction mixture. The solution was heated to reflux for an additional 2 hours and cooled to room temperature, whereupon crude formamidine precipitated. Trituration with cold hexanes and vacuum filtration provided pure formamidine as a colorless powder (55-85%).

Example 10

Acetic acid (0.086 mL, 1.5 mmol) was added to a round bottom flask charged with 2,6-difluoroaniline (3 mL, 30 mmol) and triethyl orthoformate (5 mL, 30 mmol). A vigreux column was attached and the solution was heated with stirring to 120° C. for 2 hours. 2,4,6-trimethylaniline (4.22 mL, 30 mmol) was then added to the reaction mixture. The solution was heated to reflux for an additional 2 hours and cooled to room temperature, whereupon crude product precipitated. Trituration with cold hexanes and vacuum filtration provided pure N-(2,6-difluorophenyl)-N'(mesityl)-formamidine (5.35 g, 65%) as a colorless powder.

Example 11

Formamidines were Regenerated from Formamidine hydrochlorides according to the method described below. Pyridine (an amount necessary for solvation) was added to a round bottom flask charged with formamidine hydrochloride. The solution was stirred for approximately 5 minutes then diluted with a large excess of water. The precipitated formamidine was collected by vacuum filtration, washed with hexanes and dried in vacuo.

Example 12

Pyridine (2 mL) was added to a round bottom flask charged with N,N'-dimesitylformamidine hydrochloride (0.27 g, 0.85 mmol). The solution was stirred for 5 minutes then diluted with water (10 mL), whereupon crude product precipitated. The precipitate was collected by vacuum filtration, washed with cold hexanes (5 mL) and dried in vacuo to afford N,N'-dimesitylformamidine (0.24 g, 84%) as a colorless powder.

Method C1: Dichloroethane (5 equiv) was added to a schlenk flask charged with substituted aniline (2 equiv) and triethyl orthoformate (1 equiv). The tube was evacuated until solvent began to bubble and then sealed and heated with stirring to 120° C. for 24 hours. The reaction mixture was then cooled to room temperature, diluted with solvent (acetone or hot toluene), and the precipitated imidazolinium chloride was collected by vacuum filtration, washed with excess solvent and dried in vacuo. Upon sitting overnight, the formamidine hydrochloride precipitated from the filtrate.

Example 13

According to method C1, dichloroethane (2.23 mL) was added to a schlenk flask charged with 2,4,6-trimethylaniline (1.64 mL, 11.66 mmol) and triethyl orthoformate (0.97 mL, 5.83 mmol). The tube was evacuated until solvent began to bubble and then sealed and heated with stirring to 120° C. for 24 hours. The reaction mixture was then cooled, added to toluene (50 mL) and then brought to reflux. While still hot, the precipitate was collected by vacuum filtration, washed with toluene (5 mL) and dried in vacuo to afford 1,3-dimesitylimidazolinium chloride (0.89 g, 45%) as a light peach powder.

The filtrate was allowed to sit overnight to allow for precipitation of N,N'-dimesitylformamidine hydrochloride. The precipitate was collected by vacuum filtration, washed with hexanes (5 mL) and dried in vacuo to afford N,N'-dimesitylformamidine hydrochloride (0.65 g, 35%) as colorless crystals.

Example 14

2,4,6-trimethylaniline (TMA; 2 equivalents), triethyl orthoformate (TEOF; 1.1 equivalents), acetic acid (AcOH; 0.05 equivalents), and a magnetic stir bar were charged to a 3-neck round-bottomed flask. The flask was fitted with a thermowell, a distillation head, and a glass stopper. The distillation head was connected to a Liebig condenser, which was in turn connected to a receiving vessel to collect the ethanol evolved during the reaction. The flask was heated in an oil bath to 110° C. for 6 hours during which time the mixture became a solid mass. Reaction progress was confirmed by GC analysis. When the reaction was complete, 1,2-dibromoethane (DBE) and toluene (1.4 equivalents by weight relative to the theoretical amount of DMFA) were added to dissolve the resultant N,N'-dimesitylformamidine (DMFA). The Hunig base, diisopropylethylamine (DIPA; 1.1 equivalents relative to the theoretical amount of DMFA), was then added to the flask. The mixture was heated at 110° C. for 24 hours. The heating was stopped and the content was allowed to cool to 100° C. Cold toluene (0-10° C., half of the amount of toluene used earlier) was added to the flask. The slurry was further cooled to 50° C. The solid was collected by filtration. The flask was rinsed with acetone and more solid was collected by filtration. The solids were combined and washed with the immiscible mixture of hexane/water (10/1), followed by acetone wash. The solid was dried in a vacuum oven at room temperature for 16 h and at 40° C. for 8 h. Experimental conditions and results are summarized in Table 6.

TABLE 6

One-Step Synthesis of 1,3-Dimesitylimidazolinium Bromide

| Entry | TMA (mole) | DBE (mole) | DBE/DMFA (mole/mole) | Yield (%) |
|---|---|---|---|---|
| a | 0.94 | 0.52 | 1.1 | 71 |
| b | 8.7 | 5.22 | 1.2 | 79 |

Example 15

2,4,6-trimethylaniline (TMA; 2 equivalents), triethyl orthoformate (TEOF; 1.1 equivalents), acetic acid (AcOH; 0.05 equivalents), and a magnetic stir bar were charged to a 3-neck round-bottomed flask. The flask was fitted with a thermowell, a distillation head, and a glass stopper. The distillation head was connected to a Liebig condenser, which was in turn connected to a receiving vessel to collect the ethanol evolved during the reaction. The flask was heated in an oil bath to a desired temperature for 6 hours during which time the mixture became a solid mass. Reaction progress was confirmed by GC analysis. When the reaction was complete, 1,2-dichloroethane (DCE; 18-19 equivalents relative to the theoretical amount of DMFA) was added to dissolve the resultant N,N'-dimesitylformamidine (DMFA). The Hunig's base, diisopropylethylamine (DIPA; 1.1 equivalents relative to the theoretical amount of DMFA), was then added to the flask. The mixture was heated to a temperature between 100-120° C. for 50 hours. DCE was stripped off by distillation. Toluene was added to the mixture, and the flask was allowed to cool. Acetone was added and the solid was collected by filtration. The solid was dried in a vacuum oven at room temperature for 16 h and at 40° C. for 8 h. Experimental conditions and results are summarized in Table 7.

TABLE 7

One-Step Synthesis of 1,3-Dimesitylimidazolinium Chloride

| | First Step | | Second Step | | |
|---|---|---|---|---|---|
| Entry | TMA (mole) | Temp. (° C.) | DCE (equivs.) | Temp. (° C.) | Yield (%) |
| A | 0.20 | 120 | 19 | 100 | 64 |
| B | 0.20 | 120 | 18 | 100 | 79 |
| C | 10.87 | 100 | 19 | 120 | 73 |
| D | 47.11 | 90 | 18 | 100 | 79 |

Method A2: Diisopropylethylamine (0.96 mL, 5.5 mmol, 1.1 equiv) was added to a stirred solution of formamidine (5 mmol, 1 equiv) and dichloroethane (3.8 mL, 50 mmol, 10 equiv) in a Schlenk tube. The tube was evacuated until the solvent began to bubble, then sealed under static vacuum and heated to 120° C. for 24-168 hours. The reaction mixture was then cooled to room temperature, and excess dichlorooethane was removed in vacuo. The residue was triturated with acetone or hot toluene, and the product was collected by vacuum filtration, washed with excess solvent and dried in vacuo, providing pure product as a colorless powder (85-95%). Upon sitting overnight, the diisopropylethylamine hydrochloride precipitated from the filtrate.

Method B2: Dichloroethane (7.6 mL, 100 mmol, 10 equiv) was added to a Schlenk flask charged with formamidine (10 mmol, 1 equiv). The tube was evacuated until the solvent began to bubble, then sealed under static vacuum and heated to 120° C. for 24-168 hours. The reaction mixture was then cooled to room temperature, and excess dichlorooethane was removed in vacuo. The residue was triturated with acetone or hot toluene, and the product was collected by vacuum filtration, washed with excess solvent and dried in vacuo, providing pure product as a colorless powder (85-95%). Upon sitting overnight, the formamidine hydrochloride precipitated from the filtrate.

Method C2: Dichloroethane (1.9 mL, 25 mmol, 5 equiv) was added to a Schlenk flask charged with the aniline (10 mmol, 2 equiv) and triethyl orthoformate (0.83 mL, 5 mmol, 1 equiv). The tube was evacuated until solvent began to bubble, then sealed under static vacuum and heated to 120° C. for 24-36 hours. The reaction mixture was then cooled to room temperature. Unreacted substrates were then removed in vacuo. The residue was triturated with acetone or hot toluene, and the product was collected by vacuum filtration, washed with excess solvent and dried in vacuo, providing pure product as a colorless powder (85-95%). Upon sitting overnight, the formamidine hydrochloride precipitated from the filtrate.

Example 16

1,3-Bis(2,4,6-trimethylphenyl)-imidazolinium chloride (1b) was prepared according to methods A2 (92%), B2 (49%), and C2 (45%). in 24 hours. The product was collected as a white solid after trituration with boiling toluene. The NMR data are in accordance with those reported. (A. J. Arduengo III et al. Tetrahedron 1999, 55, 14523-14534.)

Example 17

1,3-Bis(2-methylphenyl)-imidazolinium chloride (2b) was prepared according to methods A2 (43%), B2 (48%), and C2 (26%). in 24 hours. The product was collected as a white solid after trituration with acetone. The NMR data are in accordance with those reported. (Stewart, I. C.; Ung, T.; Pletnev, A. A.; Berlin, J. M.; Grubbs, R. H.; Schrodi, Y. Org. Lett. 2007, 9, 1589-1592.)

Example 18

1,3-Bis(2,6-diisopropylphenyl)-imidazolinium chloride (3b) was prepared according to methods A2 (91%), B2 (46%), and C2 (42%). in 36 hours. The product was collected as a white solid after trituration with minimal acetone. The NMR data are in accordance with those reported. (A. J. Arduengo III et al. Tetrahedron 1999, 55, 14523-14534.)

Example 19

1,3-Bis(2-tert-butylphenyl)-imidazolinium chloride (4b) was prepared according to methods A2 (91%) and B2 (46%), in 168 hours (7 days). The product was collected as a white solid after trituration in acetone. $^1$H NMR (CDCl$_3$): δ 1.46 [s, 18H], 4.86 [s, 4H], 7.35-7.50 [m, 6H], 7.97 [s, 1H], 8.70 [br, 2H]. $^{13}$C{$^1$H} NMR (CDCl$_3$): δ 32.36, 35.96, 56.68, 128.21, 128.98, 130.93, 132.43, 134.14, 146.28, 159.19. HRMS (FAB$^+$) calculated for C$_{23}$H$_{31}$N$_2$ [M$^+$] 335.2487, observed 335.2479.

Example 20

1-(2,6-difluorophenyl)-3-(2,4,6-trimethylphenyl)-imidazolinium chloride (5b) was prepared according to methods A2 (75%) and B2 (41%), in 36 hours. The product was collected as a white solid after trituration with acetone. The NMR data are in accordance with those reported. (Vougioukalakis, G. C.; Grubbs, R. H.; Organometallics 2007, 26, 2469-2472.)

Example 21

1-(2,6-diisopropylphenyl)-3-(2-methylphenyl)-imidazolinium chloride (6b) was prepared according to methods A2 (80%) and B2 (43%), in 24 hours. The product was collected as a white solid after trituration with acetone. $^1$H NMR (CDCl$_3$): δ δ 1.22 [d, 6H, J$_{HH}$=6.6 Hz], 1.28 [d, 6H, J$_{HH}$=6.6 Hz], 2.41 [s, 3H], 3.05 [sept, 2H, J$_{HH}$=6.6 Hz], 4.44-4.52 [m, 2H], 4.76-4.83 [m, 2H], 7.18-7.28 [m, 5H], 7.36-7.41 [m, 1H], 7.6-7.63 [m, 1H], 9.15 [s, 1H]. $^{13}$C{H} NMR (CDCl$_3$): δ 18.16, 24.07, 25.18, 28.83, 53.25, 54.43, 124.83, 126.05, 127.72, 129.83, 131.13, 131.87, 133.15, 134.18, 146.31, 158.58. HRMS (FAB$^+$) calculated for C$_{25}$H$_{29}$N$_2$ [M$^+$] 321.2331, observed 321.2342.

General Procedure to Isolate and Purify 1,3-bis(2,4,6-trimethylphenyl)imidazolinium chloride (sIMes-HCl) and sIMes-HBr From the reaction mixture of sIMes-HCl and DIPA-HCl:
Because large excess of DCE (10-20 eq) was used, it was necessary to remove DCE from the solution at 80-100° C. When the mixture became slurry, small amount of toluene was added and mixture was stirred at 100° C. The mixture was subject to vacuum again in order to completely remove DCE at 110° C. After removal of DCE, toluene was added and the slurry was stirred at 100° C. Once cooled to 60° C., the slurry was filtered and the solid was washed with acetone. The solid was collected and dried in a vacuum oven. This procedure was applicable to either small or large scale (0.025 mol to 50 mol).

From the Reaction Mixture of sIMes-HBr and DIPA-HBr:
A. Large Scale (4.35 mol): After the completion of the reaction, the reaction mixture was cooled at 50-60° C. The slurry was filtered in a Nutch filter. Hexane/Water (10/1 by volume) was added and the slurry was manually stirred. The liquid was filtered off and the solid was further washed with acetone. The solid was dried in a vacuum oven.

B. Small Scale (0.1 mol to 1.0 mol): It was the same as the large scale isolation except the hexane/water wash was skipped.

Discussion: Basically the reaction mixture at the end of the reaction consists of two salts, namely sIMes-HX and DIPA-HX (X=Cl or Br). The principle to separate the two salts is the solubility in different solvents at different temperature. The following table provides the basis for the separation.

|  | 100 C. | Room Temperature | | | |
| --- | --- | --- | --- | --- | --- |
|  | Toluene | Toluene | Acetone | Hexane | Water |
| sIMes-HCl |  | not soluble | slightly soluble | not soluble | slightly soluble |
| i-Pr2NEt—HCl | soluble | not soluble | very soluble | not soluble | very soluble |
| sIMes-HBr |  | not soluble | slightly soluble | not soluble | slightly soluble |
| i-Pr2NEt—HBr | soluble | not soluble | soluble | not soluble | very soluble |

The claimed invention is:

1. A method of preparing a compound of formula (III), comprising the steps of:
reacting a formamidine of formula (I) with a compound of formula (II) to form a compound of formula (III), according to the following reaction:

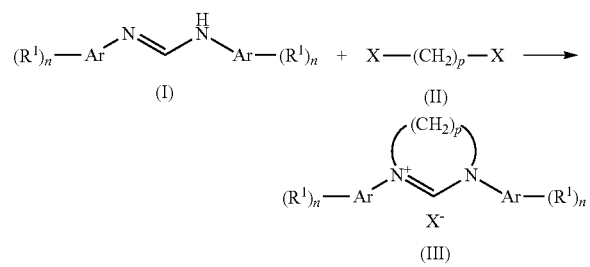

wherein:
Ar in each occurrence is independently selected from the group consisting of phenyl, naphthyl and anthracenyl;
R$^1$ in each occurrence is independently selected from the group consisting of C$_1$-C$_6$ alkyl; C$_1$-C$_6$ alkoxy; halogen; aryl; —Si(R$^2$)$_3$, wherein each R$^2$ is independently a C$_1$-C$_6$ alkyl; and —NR$^3$R$^4$, wherein R$^3$ and R$^4$ are independently a $C_1$-$C_6$ alkyl or wherein $R^3$ and $R^4$, together with the nitrogen carrying them form a 5- or 6-membered heterocyclic ring;

X is a leaving group;

each n ranges from 0 to 5 when Ar is phenyl, from 0 to 7 when Ar is naphthyl, and from 0-9 when Ar is anthracenyl; and p is 2.

2. A method of claim 1, wherein:

Ar is phenyl;

$R^1$ in each occurrence is independently selected from the group consisting of $C_1$-$C_4$ alkyl; $C_1$-$C_4$ alkoxy; fluorine; chlorine; phenyl; naphthyl, —Si($R^2$)$_3$, wherein each $R^2$ is independently a $C_1$-$C_4$ alkyl; and —NR$^3$R$^4$, wherein $R^3$ and $R^4$ are independently a $C_1$-$C_4$ alkyl;

X is halogen, mesylate, tosylate, perchlorate, sulfate, or triflate; and each n ranges from 1 to 3.

3. A method of claim 2, wherein $R^1$ in each occurrence is independently selected from the group consisting of methyl, ethyl, iso-propyl, tert-butyl or fluorine;

X is chlorine or bromine; and n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring.

4. A method of claim 1, wherein the reaction occurs in the presence of a non-nucleophilic base, wherein the non-nucleophilic base is selected from the group consisting of di-isopropylethylamine, 2,6-dimethylpiperidine, 2,2,6,6-tetramethylpiperidine, di-isopropylamine, Li salt of di-isopropylamide, and bis(trimethylsilyl)amine.

5. A method of claim 1, wherein the reaction is a solvent-free reaction.

6. A method of preparing a compound of formula (III) of claim 1 further comprising the step of:

reacting one or more compound of formula (IV) and trialkyl orthoformate of formula (V) to form a formamidine of formula (I) according to the following reaction:

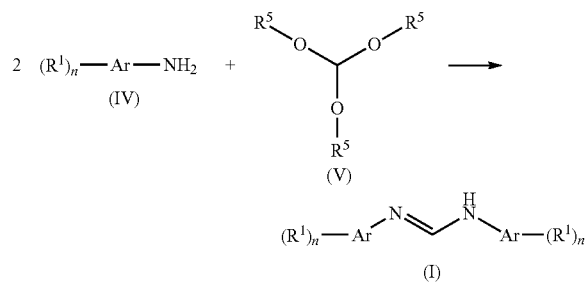

wherein:

Ar is selected from the group consisting of phenyl, naphthyl and anthracenyl;

$R^1$ in each occurrence is independently selected from the group consisting of $C_1$-$C_6$ alkyl; $C_1$-$C_6$ alkoxy; halogen; aryl; —Si($R^2$)$_3$, wherein each $R^2$ is independently a $C_1$-$C_6$ alkyl; and —NR$^3$R$^4$, wherein $R^3$ and $R^4$ are independently a $C_1$-$C_6$ alkyl or wherein $R^3$ and $R^4$, together with the nitrogen carrying them form a 5- or 6-membered heterocyclic ring;

each n ranges from 0 to 5 when Ar is phenyl, from 0 to 7 when Ar is naphthyl, and from 0-9 when Ar is anthracenyl;

$R^5$ is a $C_1$-$C_6$ alkyl; and when more than one compound of formula (IV) is used, each Ar is different and the compounds of formula (IV) are reacted sequentially with the trialkyl orthoformate of formula (V); and p is 2.

7. A method of claim 6, wherein:

Ar is phenyl;

$R^1$ in each occurrence is independently selected from the group consisting of $C_1$-$C_4$ alkyl; $C_1$-$C_4$ alkoxy; fluorine; chlorine; phenyl; naphthyl; —Si($R^2$)$_3$, wherein each $R^2$ is independently a $C_1$-$C_4$ alkyl; and —NR$^3$R$^4$, wherein $R^3$ and $R^4$ are independently a $C_1$-$C_4$ alkyl;

X is halogen, mesylate, tosylate, perchlorate, sulfate, or triflate;

each n ranges from 1 to 3; and $R^5$ is a $C_1$-$C_4$ alkyl 3.

8. A method of claim 7, wherein $R^1$ in each occurrence is independently selected from the group consisting of methyl, ethyl, iso-propyl, tert-butyl or fluorine;

X is chlorine or bromine;

n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring; and $R^5$ is ethyl.

9. A method of claim 6, wherein Ar in each occurrence is the same.

10. A method of claim 9, wherein:

Ar is phenyl;

$R^1$ in each occurrence is independently selected from the group consisting of $C_1$-$C_4$ alkyl; $C_1$-$C_4$ alkoxy; fluorine; chlorine; phenyl; naphthyl; —Si($R^2$)$_3$, wherein each $R^2$ is independently a $C_1$-$C_4$ alkyl; and —NR$^3$R$^4$, wherein $R^3$ and $R^4$ are independently a $C_1$-$C_4$ alkyl;

X is halogen, mesylate, tosylate, perchlorate, sulfate, or triflate;

each n ranges from 1 to 3; and $R^5$ is a $C_1$-$C_4$ alkyl.

11. A method of claim 10, wherein $R^1$ in each occurrence is independently selected from the group consisting of methyl, ethyl, iso-propyl, tert-butyl or fluorine;

X is chlorine or bromine;

n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring; and $R^5$ is ethyl.

12. A method of claim 6, wherein more than one compound of formula (IV) is used and Ar in each occurrence is different.

13. A method of claim 12, wherein:

$R^1$ in each occurrence is independently selected from the group consisting of $C_1$-$C_4$ alkyl; $C_1$-$C_4$ alkoxy; fluorine; chlorine; phenyl; naphthyl; —Si($R^2$)$_3$, wherein each $R^2$ is independently a $C_1$-$C_4$ alkyl; and —NR$^3$R$^4$, wherein $R^3$ and $R^4$ are independently a $C_1$-$C_4$ alkyl;

X is halogen, mesylate, tosylate, perchlorate, sulfate, or triflate;

each n ranges from 1 to 3; and $R^5$ is a $C_1$-$C_4$ alkyl.

14. A method of claim 13, wherein
R$^1$ in each occurrence is independently selected from the group consisting of methyl, ethyl, iso-propyl, tert-butyl or fluorine;
X is chlorine or bromine;
n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring; and
R$^5$ is ethyl.

15. A one-step method of preparing a compound of formula (III) comprising the step of:
reacting a compound of formula (IV) and trialkyl orthoformate of formula (V) in the presence of a compound of formula (II) to form a compound of formula (III), according to the following reaction:

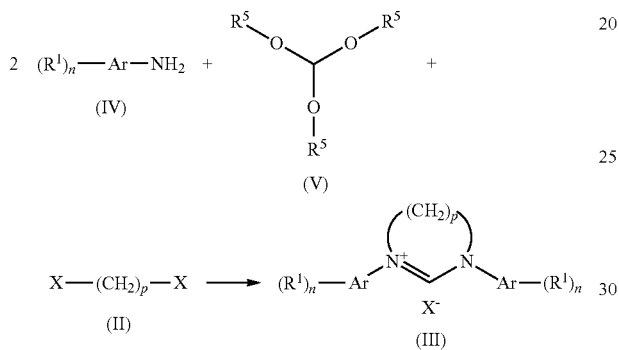

wherein:
Ar is selected from the group consisting of phenyl, naphthyl and anthracenyl;
R$^1$ in each occurrence is independently selected from the group consisting of C$_1$-C$_6$ alkyl; C$_1$-C$_6$ alkoxy; halogen; aryl; —Si(R$^2$)$_3$, wherein each R$^2$ is independently a C$_1$-C$_6$ alkyl; and —NR$^3$R$^4$, wherein R$^3$ and R$^4$ are independently a C$_1$-C$_6$ alkyl or wherein R$^3$ and R$^4$, together with the nitrogen carrying them form a 5- or 6-membered heterocyclic ring;
X is a leaving group;
each n ranges from 0 to 5 when Ar is phenyl, from 0 to 7 when Ar is naphthyl, and from 0-9 when Ar is anthracenyl;
R$^5$ is a C$_1$-C$_6$ alkyl; and
p is 2.

16. A method of claim 15, wherein:
Ar is phenyl;
R$^1$ in each occurrence is independently selected from the group consisting of C$_1$-C$_4$ alkyl; C$_1$-C$_4$ alkoxy; fluorine; chlorine; phenyl; naphthyl; —Si(R$^2$)$_3$, wherein each R$^2$ is independently a C$_1$-C$_4$ alkyl; and —NR$^3$R$^4$, wherein R$^3$ and R$^4$ are independently a C$_1$-C$_4$ alkyl;
X is halogen, mesylate, tosylate, perchlorate, sulfate, or triflate;
each n ranges from 1 to 3; and
R$^5$ is a C$_1$-C$_4$ alkyl.

17. A method of claim 15, wherein
R$^1$ in each occurrence is independently selected from the group consisting of methyl, ethyl, iso-propyl, tert-butyl or fluorine;
X is chlorine or bromine;
n is 1 with ortho, meta, or para substitution on the phenyl ring; n is 2 with di-ortho, di-meta, ortho and meta, or ortho and para substitution on the phenyl ring; or n is 3 with di-ortho and para, or di-meta and para substitution on the phenyl ring; and
R$^5$ is ethyl.

* * * * *